(12) United States Patent
Cornish et al.

(10) Patent No.: US 6,494,891 B1
(45) Date of Patent: Dec. 17, 2002

(54) ULTRASONIC ANGIOPLASTY TRANSMISSION MEMBER

(75) Inventors: Wayne E. Cornish, Fallbrook, CA (US); Robert C. Esselstein, Fallbrook, CA (US); Sepehr Fariabi, Fremont, CA (US); Henry Nita, Mission Viejo, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/474,953

(22) Filed: Dec. 30, 1999

(51) Int. Cl.[7] .............................................. A61B 17/32
(52) U.S. Cl. ...................................... 606/169; 604/22
(58) Field of Search ............................... 600/585, 434, 600/435; 606/191, 194, 195, 169; 604/22

(56) References Cited

U.S. PATENT DOCUMENTS

| | | | |
|---|---|---|---|
| 4,721,117 A | | 1/1988 | Mar et al. ................... 128/772 |
| 4,870,953 A | | 10/1989 | DonMicheal et al. ......... 128/24 |
| 4,925,445 A | * | 5/1990 | Sakamoto et al. .......... 604/281 |
| 5,163,421 A | | 11/1992 | Bernstein et al. .......... 128/24.1 |
| 5,267,954 A | * | 12/1993 | Nita .............................. 604/22 |
| 5,365,943 A | * | 11/1994 | Jansen ......................... 600/585 |
| 5,368,557 A | | 11/1994 | Nita et al. ...................... 604/22 |
| 5,380,274 A | * | 1/1995 | Nita ............................. 606/169 |
| 5,382,228 A | * | 1/1995 | Nita et al. ...................... 604/22 |
| 5,397,293 A | * | 3/1995 | Alliger et al. |
| 5,397,301 A | * | 3/1995 | Pflueger et al. ................ 604/22 |
| 5,405,318 A | * | 4/1995 | Nita ............................. 604/22 |
| 5,411,476 A | | 5/1995 | Abrams et al. ................ 604/95 |
| 5,427,118 A | * | 6/1995 | Nita et al. ....................... 601/2 |
| 5,542,917 A | | 8/1996 | Nita et al. ...................... 604/22 |
| 5,606,979 A | * | 3/1997 | Hodgson ..................... 600/585 |
| 5,735,811 A | | 4/1998 | Brisken ........................ 604/22 |
| 5,827,201 A | | 10/1998 | Samson et al. ............. 600/585 |
| 5,846,218 A | | 12/1998 | Brisken et al. ............... 604/22 |
| 5,989,208 A | | 11/1999 | Nita ............................. 604/22 |
| 6,007,514 A | | 12/1999 | Nita ............................. 604/22 |
| 6,290,656 B1 | * | 9/2001 | Boyle et al. ................. 600/585 |
| 6,296,620 B1 | * | 10/2001 | Gesswein et al. ............. 604/22 |

* cited by examiner

*Primary Examiner*—Kevin T. Truong
(74) *Attorney, Agent, or Firm*—Fulwider Patton Lee & Utecht, LLP

(57) ABSTRACT

The ultrasonic angioplasty transmission wire has regions of reduced cross-sectional diameter to improve flexibility of the ultrasonic angioplasty transmission wire and to compensate for degradation of longitudinal displacement due to acoustic losses along the length of the ultrasonic angioplasty transmission wire. One or more constraining members are disposed on the ultrasonic angioplasty transmission wire at one or more of the regions of reduced cross-sectional diameter where transverse vibration of ultrasonic energy transmitted by the ultrasound transmission wire is amplified, to constrain transverse vibration at these areas to reduce stress and reduce fracturing, while allowing longitudinal movement. The transmission wire has an elongated shaft including, in atomic percent, from about 28 to about 52 percent nickel, from about 48 to about 52 percent titanium, and up to about 20 percent of at least one alloying element selected from the group consisting of palladium, chromium, and hafnium.

41 Claims, 4 Drawing Sheets

ULTRASONIC ANGIOPLASTY TRANSMISSION MEMBER

BACKGROUND

This invention relates generally to medical devices, and more particularly concerns an improved ultrasound transmission member for use in an ultrasonic catheter for treatment of blockages of hollow anatomical structures.

In typical percutaneous transluminal coronary angioplasty (PTCA) procedures, a guiding catheter having a preformed distal tip is percutaneously introduced into the cardiovascular system of a patient through the brachial or femoral arteries and is advanced therein until the distal tip thereof is in the ostium of the desired coronary artery. A guide wire and a dilatation catheter having a balloon on the distal end thereof are introduced through the guiding catheter with the guide wire slidably disposed within an inner lumen of the dilatation catheter. The guide wire is first advanced into the patient's coronary vasculature until the distal end thereof crosses the lesion to be dilated and then the dilatation catheter is advanced over the previously introduced guide wire until the dilatation balloon is properly positioned across the lesion. The balloon may then be inflated to treat the lesion. Thereafter, a stent device may be located at the treated lesion, if deemed necessary.

In "ultrasonic" angioplasty, an ultrasonic angioplasty catheter is similarly advanced to an area of vascular blockage, and mechanical vibration at ultrasonic frequencies, generated typically by a piezoceramic transducer, is delivered along an ultrasonic angioplasty transmission member or wire to a distal catheter tip. When the distal catheter tip is abutted against intravascular blockage, the vibration of the distal end of the ultrasonic angioplasty transmission member removes the obstruction by mechanical impact and cavitation. However, such ultrasonic angioplasty transmission members frequently suffer from high-cycle fatigue, which can result in fracturing or breakage of the members during use.

Ultrasonic angioplasty transmission members are commonly connected to an extra-corporeal source of ultrasonic energy, so that it is generally necessary to deliver the ultrasonic energy over a relatively long distance, such as approximately 150 cm, to the intravascular blockage to be treated. Over such a distance, the ultrasonic energy attenuates as it passes along the length of the ultrasonic angioplasty transmission member resulting in a loss of system efficiency. To compensate for the loss, a greater amount of acoustical energy is delivered to the ultrasonic angioplasty transmission member at its proximal end than what actually reaches the treatment site. This delivery of higher levels of acoustic energy can increase fatigue and the chances of fracturing and breakage of the ultrasonic angioplasty transmission member during use. It is therefore desirable to provide an ultrasonic angioplasty transmission member that has a lower loss of the ultrasonic energy transmitted by the member so that lower levels of energy may be applied to the member.

In ultrasonic angioplasty techniques, accurate positioning of the ultrasound transmission member in the vasculature system to be treated requires a highly flexible ultrasonic delivery system with a low profile, especially for coronary ultrasonic angioplasty procedures, so that the catheter can more easily navigate the various vascular passages to be advanced to the occlusion. Nickel-titanium superelastic alloys have been useful in these respects as an ultrasound transmission member. Tapering or narrowing the distal end of an ultrasound transmission member to enhance flexibility of the ultrasound transmission member at its distal end is known from U.S. Pat. No. 5,304,115 (Pflueger et al.). While such tapering or narrowing typically decreases the rigidity and improves the bendability of the ultrasound transmission member, a significant increase in amplitude of the ultrasonic energy occurs at the tapered or narrowed region. Such an increase in amplitude can cause an increased likelihood of fracturing or breakage of the ultrasound transmission member at that point during use.

While it is known to harden ultrasonic angioplasty transmission members to reduce fracturing or breakage, as disclosed in U.S. Pat. No. 5,304,115 (Pflueger et al.), by providing a hard coating or skin, it would be desirable to constrain transverse vibration at narrowed or tapered areas of an ultrasonic angioplasty transmission member to reduce stress and to lessen the chances of fracturing at such areas where amplification of ultrasonic energy can occur, while still allowing longitudinal movement. Additionally, it has been found that providing a hard coating or skin to reduce stress and attempt to prevent fracturing can contribute to attenuation of vibration of the ultrasonic angioplasty transmission member and inhibit longitudinal movement.

Hence those skilled in the art have recognized a need for an ultrasound transmission member providing improved characteristics of strength, fatigue resistance, elasticity, and energy transmission for an ultrasonic delivery system for use in the treatment of intravascular blockages. It is also desirable that measures to reduce fracturing or breakage of such ultrasonic angioplasty transmission members not interfere with properties such as sonic propagation, tensile strength, and flexibility to navigate sharp bends and curves in the vasculature. The present invention fulfills these needs and others.

SUMMARY OF THE INVENTION

Briefly, and in general terms, the present invention is directed to an improved ultrasound transmission member for use in an ultrasonic angioplasty device, the ultrasound transmission member having a proximal end configured to be connected to an ultrasound transducer and a distal end for applying ultrasonic energy to an area of vascular blockage, and the ultrasound transmission member having a distal portion with at least one amplification region of reduced cross-sectional diameter where transverse vibration of ultrasonic energy transmitted by the ultrasound transmission member is amplified, the ultrasound transmission member comprising a constraining member disposed around the amplification region to reduce transverse vibration at the amplification region, to thereby lower stress and reduce fractures of the ultrasound transmission member while allowing longitudinal movement of the ultrasound transmission member.

In another aspect, the invention is directed to an ultrasonic angioplasty catheter device comprising an elongate flexible catheter having a proximal end, a distal end, and at least one lumen extending longitudinally therethrough, the catheter device comprising an ultrasound transmission member extending through aid lumen and having a distal end with a head for applying ultrasonic energy to an occlusive lesion, and a proximal end configured to be connected to an ultrasound generating device, the ultrasound transmission member having a distal portion with at least one amplification region of reduced cross-sectional diameter where transverse vibration of ultrasonic energy transmitted by the ultrasound transmission member is amplified wherein the ultrasound transmission member comprises a constraining member disposed around the amplification region to reduce transverse vibration at the amplification region to thereby lower stress and reduce fractures of the ultrasound transmission member while allowing longitudinal movement of the ultrasound transmission member.

In more detailed aspects, the ultrasound transmission member comprises a first generally cylindrical section of the ultrasound transmission member having a first cross-sectional diameter, and a second generally cylindrical section of the ultrasound transmission member distal to the first section and having a second cross-sectional diameter that is smaller than the first cross-sectional diameter, the amplification region being formed at a proximal portion of the second generally cylindrical section. The ultrasound transmission member further comprises a plurality of generally cylindrical sections, each of the plurality of generally cylindrical sections having reduced cross-sectional diameter relative to a proximal adjacent section resulting in a plurality of amplification regions in the cylindrical sections of reduced cross-sectional diameter, wherein the constraining member is disposed around at least one of the amplification regions of the reduced diameter cylindrical sections to reduce transverse vibration at the amplification regions. The ultrasound transmission member further comprises a conically tapered section interposed between the first and second cylindrical sections.

In further aspects, the ultrasound transmission member further comprises a plurality of conically tapered sections interposed between adjacent ones of the plurality of generally cylindrical sections. Additionally, the ultrasound transmission member comprises an end cylindrical section, a penultimate cylindrical section immediately adjacent and proximal to the end cylindrical section, and a cylindrical section immediately adjacent and proximal to the penultimate cylindrical section having a larger diameter than the penultimate cylindrical section, the end cylindrical section having a cross-sectional diameter that is larger than the penultimate cylindrical section, and the constraining member being disposed over the end cylindrical section and over the penultimate cylindrical section and over the larger diameter cylindrical section immediately adjacent and proximal to the penultimate cylindrical section.

In yet further detail, the ultrasound transmission member comprises an end cylindrical section, a penultimate cylindrical section immediately adjacent and proximal to the end cylindrical section, the end cylindrical section having a cross-sectional diameter that is larger than the penultimate cylindrical section, a larger cylindrical section immediately adjacent and proximal to the penultimate cylindrical section having a larger diameter than the penultimate cylindrical section, and a conically tapered section immediately adjacent and proximal to the larger cylindrical section, and the constraining member being disposed over the end cylindrical section and over the penultimate cylindrical section and over the larger diameter cylindrical section immediately adjacent and proximal to the penultimate cylindrical section and over the conically tapered section immediately adjacent and proximal to the larger diameter cylindrical section.

In more detailed aspects, the constraining member is formed of a non-metallic material, such as shrink tubing, rubber, or plastic.

In other detailed aspects, the ultrasonic transmission member is in a fixed position within the catheter lumen and is connected to a distal head positioned on the distal end of said ultrasound member such that the distal head extends beyond the distal end of the catheter. The distal head comprises a larger diameter distal portion positioned beyond the distal end of the catheter and a smaller diameter portion located between the distal portion and the ultrasound transmission member and extending within the catheter. The ultrasound transmission member is formed at least partially of a superelastic metal alloy. In another aspect, the ultrasound transmission member is formed at least partially of a shape memory alloy that exhibits superelastic properties when in its martensitic state, and in yet a further aspect, the ultrasound transmission member is formed of a nickel-titanium alloy.

In yet further aspects, the distal head comprises a guide wire aperture to permit passage of a guide wire therethrough. Also, the region of reduced cross-sectional diameter is located within 5 cm to 30 cm of the distal end of the ultrasound transmission member. The ultrasound transmission member has a smaller diameter towards its distal end and increases to a larger diameter towards its proximal end.

In further aspects in accordance with the invention, there is provided an ultrasound transmission member for use in an ultrasonic angioplasty device, the ultrasound transmission member having a proximal end configured to be connected to an ultrasound transducer and a distal end for applying ultrasonic energy to an area of vascular blockage, the ultrasound transmission member comprising an elongated shaft including, in atomic percent, from about 28 to about 52 percent nickel, from about 48 to about 52 percent titanium, and up to about 20 percent of at least one alloying element selected from the group consisting of palladium, chromium, and hafnium. In further detail, the alloying element is hafnium or palladium, and is present, in atomic percent, in a range from about 3 to about 20 percent.

In further aspects, the alloying element is present, in atomic percent, in a range from about 5 to about 11 percent. The alloying element is palladium. In another aspect, the alloying element is chromium and is present, in atomic percent, in a range up to about 3 percent.

In yet a further aspect, the alloying element is present, in atomic percent, in a range from about 0.1 to about 1.0 percent. In another detailed aspect, the alloying element is present, in atomic percent, in a range from about 0.2 to about 0.5 percent.

These and other aspects and advantages of the invention will become apparent from the following detailed description and the accompanying drawings, which illustrate by way of example, the features of the invention.

DETAILED DESCRIPTION OF THE PREFERRED EMBODIMENTS

Figure 1:
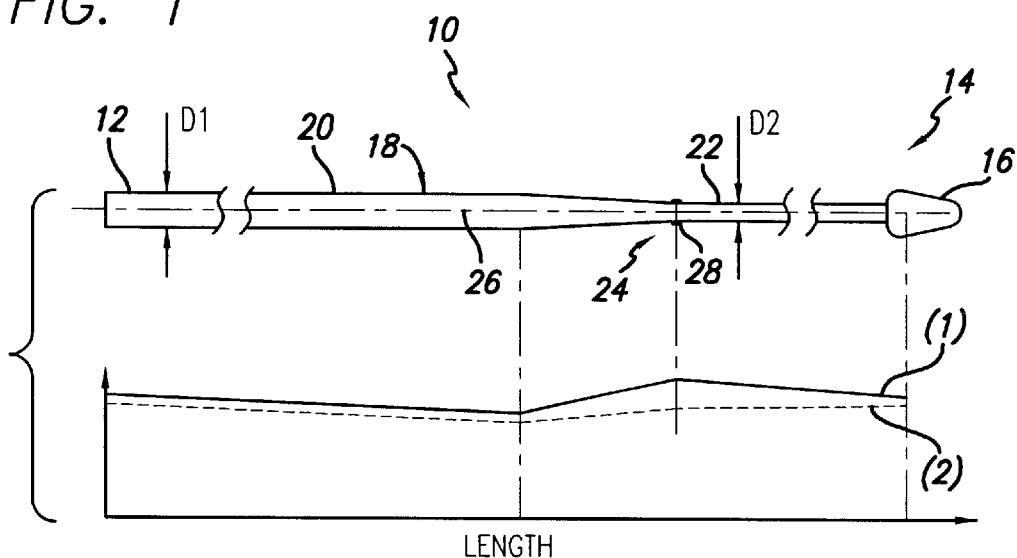
FIG. 1 is a graph of the amplitude of transverse vibration of the first embodiment of an ultrasound transmission wire shown above the graph according to the principles of the invention.

Referring now to the drawings in more detail in which like reference numerals refer to like or corresponding elements among the views, there is shown in FIG. 1 an elongate ultrasound transmission member or wire 10 that has a proximal end 12 attached to an ultrasound transducer (not shown) and a distal end 14 with a distal head 16, in this case an enlarged head, for applying ultrasonic energy to an area of vascular blockage. In a currently preferred embodiment, improved flexibility of the ultrasound transmission wire 10 is achieved by reducing the cross-sectional diameter of the ultrasound transmission wire at the distal end. Degradation of longitudinal displacement of the transmission wire due to acoustic losses along its length between its proximal end 12 and its distal end 14 is compensated for by step amplifications. The ultrasound transmission wire is stepped to a lower diameter along one or more sections of the wire, as is illustrated in FIG. 1 by the taper 26.

The ultrasound transmission wire 10 thus comprises a distal portion 18 having a first generally cylindrical section 20 with a first cross-sectional diameter D1, and a second generally cylindrical section 22 distal to the first section and having a second cross-sectional diameter D2 that is smaller than the first cross-sectional diameter D1. The second generally cylindrical section 22 has an amplification region 24 of reduced cross-sectional diameter, typically at a proximal end of the second generally cylindrical section 22 where transverse vibration of ultrasonic energy transmitted from the first generally cylindrical section is amplified. A conically tapered section 26 is preferably interposed between adjacent cylindrical sections of different diameters to provide a smooth transition area from one cylindrical section to the next. Each transition area preferably provides a smooth shift between adjacent cylindrical sections of different diameters to reduce stress concentrations due to transverse vibrations of the ultrasound transmission wire.

The regions where highest amplification occurs are generally located where the transition to a reduced diameter occurs, which is typically at the proximal end of a smaller diameter section. These areas are prone to higher longitudinal and transverse vibrations as a result of the amplification they provide. Although the longitudinal vibration is desirable for increased efficiency of transmission of ultrasonic energy from the proximal end 12 to the distal end 14 of the wire 10, the transverse vibration results in potentially damaging stress concentrations, which have an even higher potential for damage at the smaller cross-sectional areas of the ultrasonic transmission wire. It would be desirable to lessen such transverse vibrations.

Preferably, the ultrasound transmission wire is formed of a superelastic alloy of a material composition including, by atomic percent, about 28 to about 52 percent nickel, preferably from about 34 to about 49 percent nickel; from about 48 to about 52 percent titanium; and up to about 20 percent of at least one alloying element selected from the group consisting of palladium, chromium, and hafnium. When the alloying element is palladium or hafnium, the alloying element is preferably present in a range from about 3 to about 20 percent, more preferably, from about 5 to about 11 percent. When the alloying element is chromium, the alloying element is preferably present up to about 3 percent, more preferably, from about 0.1 to about 1 percent, and most preferably from about 0.2 to about 0.5 percent. Preferably, the alloying element is palladium. Of course, the alloy material composition may include further elements of improving other desirable features such as manufacturability. The alloy material of the present invention has an increased ultimate tensile strength and tensile yield strength. This increase in the ultimate tensile strength and tensile yield strength provides for an ultrasound transmission wire having at least substantially the superelasticity and kink resistance of a wire made of NITINOL and substantially the increased modulus of elasticity and tensile strength of a wire made of stainless steel.

A presently preferred method of making the final configuration of the superelastic alloy of the present invention is to cold work, preferably by drawing, a rod or tubular member having a composition according to the relative proportions described above and then heat treating the cold worked product while it is under stress to impart a shape memory thereto. Typical initial transverse dimensions of the rod or the tubular member are about 0.045 inch and about 0.25 inch respectively. If the final product is to be tubular, a small diameter ingot, e.g., 0.25 to about 1.5 inch in diameter and 5 to about 30 inches in length, may be formed into a hollow tube by extruding or by machining a longitudinal center hole therethrough and grinding the outer surface thereof smooth. Before drawing the solid rod or tubular member, it is preferably annealed at a temperature of about 500 degrees to about 750 degrees C., typically about 650 degrees C., for about 30 minutes in a protective atmosphere such as argon to relieve essentially all internal stresses. In this manner all of the specimens start the subsequent thermomechanical processing in essentially the same metallurgical condition so that products with consistent final properties are obtained. Such treatment also provides the requisite ductility for effective cold working.

The stressed relieved stock is cold worked by drawing to effect a reduction in the cross sectional area thereof at about 30 to about 70 percent. The metal is drawn through one or more dies of appropriate inner diameter with a reduction per pass of about 10 to 50 percent. Other forms of cold working can be employed such as swaging.

Following cold work, the drawn wire or hollow tubular product is heat treated at a temperature between about 350 degrees and about 600 degrees C. for about 0.5 to about 60 minutes. Preferably, the drawn wire or hollow tubular product is simultaneously subjected to a longitudinal stress between about 5 percent and about 50 percent, preferably about 10 percent to about 30 percent of the tensile strength of the material (as measured at room temperature) in order to impart a straight "memory" to the metal and to ensure that any residual stresses therein are uniform. This memory imparting heat treatment also fixes the austenite-martensite transformation temperature from the cold worked metal. By developing a straight "memory" and maintaining uniform residual stresses in the superelastic material, there is little or no tendency for an ultrasound transmission wire of this material to whip when it is torqued within a patient's blood vessel.

An alternate method for imparting a straight memory to the cold worked material includes mechanically straightening the wire or tube and then subjecting the straightened wire to a memory imparting heat treatment at a temperature of about 300 degrees to about 450 degrees C., preferably about 330 degrees C. to about 400 degrees C. The latter treatment provides substantially improved tensile properties, but it is not very effective on materials that have been cold worked above 55 percent, particularly above 60 percent. Materials produced in this manner exhibit stress-induced austenite to martensite phase transformation at very high levels of stress but the stress during the phase transformation is not nearly as constant as the previously discussed method. Conventional mechanical straightening means can be used such as subjecting the material to sufficient longitudinal stress to straighten it.

In another embodiment, the ultrasound transmission wire, which is extended longitudinally through a catheter, is formed of a heat treated superelastic alloy, such as that disclosed in U.S. Pat. No. 5,411,476 to Abrams et al. This nickel-titanium alloy, which is available from Fort Wayne Metals, in Fort Wayne, Indiana, exhibits a superelastic property in the higher temperature range, demonstrates improved strength and elasticity prior to permanent deformation, and also good acoustic properties.

The superelastic alloy consists essentially of about 40 to 49% titanium, with a balance of nickel and up to 10% of one or more additional alloying elements that can be selected from the group of up to 3% each of iron, cobalt or chromium, and up to about 10% copper and vanadium, all by atomic percent. The alloy material is preferably cold worked, preferably by drawing, to effect a size reduction of about 30% to about 70% in the transverse cross section thereof. The cold worked material can then be given a memory-imparting heat treatment at a temperature of about 350° C. to about 600° C. for about 0.5 to about 60 minutes, while maintaining longitudinal stress on the elongated portion equal to about 5% to about 50%, preferably about 10% to about 30%, of the yield stress of the material, as measured at room temperature. Another method involves mechanically straightening the wire after the cold work, and then heat treating the wire at temperatures between about 300° C. and 450° C., preferably about 330° C. to about 400° C. For more consistent final properties, it is preferred to fully anneal the stock prior to cold working so that the material will always have the same metallurgical structure at the start of cold working and will have adequate ductility for subsequent cold working. Cold working of the metal other than drawing, such as rolling or swaging, can also be employed. Another nickel-titanium alloy that may also be suitable in forming the ultrasound transmission wire contains 50.8 atomic percent nickel, and is sold under the trade name TINEL by Raychem Corporation.

While the flexibility of the ultrasound transmission wire is improved by step reductions in diameter and the degradation of the ultrasonic power due to acoustic losses presented by the length of the wire is compensated for by step amplifications at the step reductions to a smaller diameter, increased stress concentration at these regions results. These stress concentrations are preferably reduced by placing constraining members at the areas of highest amplification on the ultrasound transmission wire. As is illustrated in the generalized diagram of FIG. 1, in one presently preferred embodiment, a constraining member 28 is disposed around the amplification region 24 of the ultrasound transmission wire to reduce transverse vibration, to thereby lower stress and lower the possibility of ultrasonic wire fractures of the ultrasound transmission wire, while allowing longitudinal movement of the ultrasound transmission wire. As shown in FIG. 1, the constraining member 28 can be formed as a relatively narrow annular support or band that can be tightly disposed around an amplification region, and can be made of shrink tubing, rubber or plastic, for example, although other similar materials that can reduce transverse vibration at the amplification regions of the ultrasound transmission wire may also be suitable.

Constraining members are preferably placed firmly around the amplification regions of the ultrasound transmission wire to reduce transverse vibration at the amplification regions to lower stress and reduce the chances of ultrasonic wire fractures, while allowing longitudinal movement. The constraining members can also be extended over longer segments of increased amplification. However, placing long segments of constraining material over segments of the ultrasound transmission wire can cause an additional source of friction that can affect longitudinal acoustic transmission. Upon navigating vasculature that includes sharp bends, the internal ultrasound transmission member may come into contact with the inner wall of the catheter at the bend thus providing a place for friction to occur. Constraining members can also be applied to proximal amplification regions, such as at a connection of the ultrasonic transducer to the ultrasound transmission wire (not shown), which represents the one of the regions where the greatest amplification occurs due to a stepped reduction in diameter.

Referring to the graph of the amplitude of transverse vibration in FIG. 1, it can readily be seen from the solid line (1), showing transverse vibration along the length of the ultrasound transmission wire without a constraining member, that the amplitude of transverse vibration becomes greatest at the amplification region 24 when no constraining member is placed on the amplification region of the ultrasound transmission wire. However, as shown by the dotted line (2), showing transverse vibration along the length of the ultrasound transmission wire with a constraining member, the amplification of the amplitude of transverse vibration is greatly reduced at the amplification region 24 when a constraining member is placed on the amplification region of the ultrasound transmission wire.

As should be readily apparent, additional generally cylindrical sections can be provided in sequence in the ultrasound transmission wire 10 that are of reduced cross-sectional diameter relative to a proximal adjacent section. As will be further discussed below, the constraining member can be formed as a wider band disposed around one or more amplification regions, as well as all or a portion of one or more adjacent cylindrical sections of the ultrasound transmission wire and all or a portion of the conically tapered sections typically disposed between adjacent cylindrical sections, to reduce transverse vibration at the amplification regions.

Figure 2:
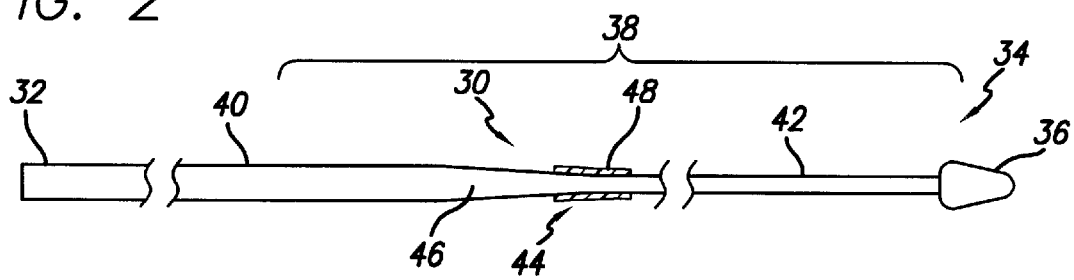
FIG. 2 is a side partial sectional view illustrating a second embodiment of an ultrasound transmission wire and a constraining member according to principles of the invention.
Figure 3:
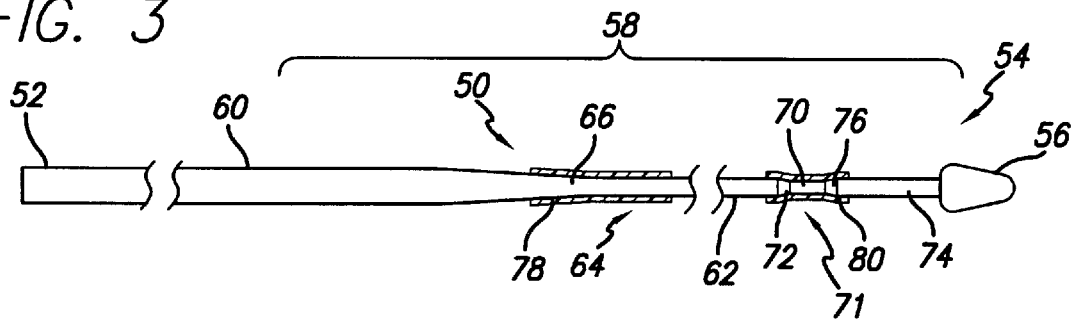
FIG. 3 is a side partial sectional view illustrating a third embodiment of an ultrasound transmission wire with multiple constraining members according to principles of the invention.
Figure 4:
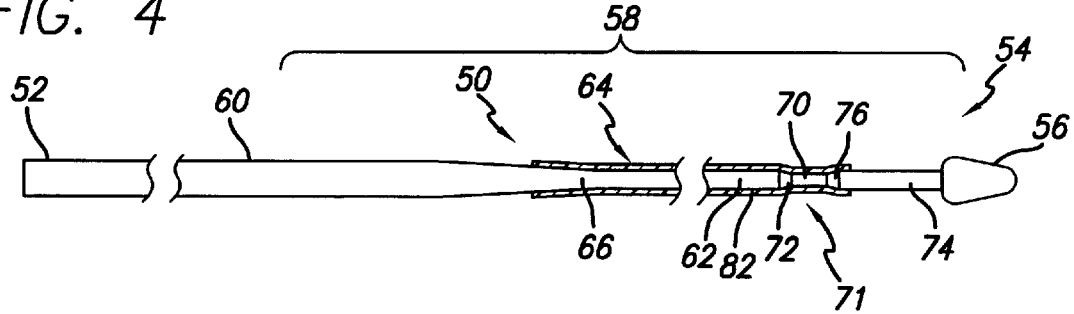
FIG. 4 is a side partial sectional view illustrating a fourth embodiment of an ultrasound transmission wire and constraining member according to principles of the invention.

As is illustrated in FIGS. 2, 3, and 4 in a presently preferred embodiment of an ultrasound transmission wire according to the invention, the ultrasound transmission wire includes multiple segments or generally cylindrical sections at its distal end, with a conically tapered transition area located between adjacent segments. Referring to FIG. 2, an ultrasound transmission wire 30 has a proximal end 32 attached to an ultrasound transducer (not shown) and a distal end 34 with a distal head 36 for applying ultrasonic energy to an area of vascular blockage. The ultrasound transmission wire comprises distal portion 38 having a first generally cylindrical section 40 with a first cross-sectional diameter, and a second generally cylindrical section 42 distal to the first section and having a second cross-sectional diameter that is smaller than the first cross-sectional diameter. The second generally cylindrical section 42 has an amplification region 44 of reduced cross-sectional diameter, typically at a proximal end of the second generally cylindrical section 42 where transverse vibration of ultrasonic energy transmitted from the first generally cylindrical section 42 is amplified. A conically tapered section 46 is preferably interposed between the first and second cylindrical sections. In the embodiment illustrated in FIG. 2, a constraining member 48 is disposed around the amplification region 44 of the ultrasound transmission wire, and extends approximately midway over the conically tapered section 46 and over a proximal portion of the second cylindrical section 42 to reduce transverse vibration.

In another presently preferred embodiment of an ultrasound transmission wire according to the invention and as illustrated in FIG. 3, an elongated ultrasound transmission member or wire 50 has a proximal end 52 attached to an ultrasound transducer (not shown) and a distal end 54 with a distal head 56 for applying ultrasonic energy to an area of vascular blockage. The ultrasound transmission wire comprises a distal portion 58 having a first generally cylindrical section 60 with a first cross-sectional diameter, and a second generally cylindrical section 62 distal to the first section and having a second cross-sectional diameter that is smaller than the first cross-sectional diameter. The second generally cylindrical section 62 has an amplification region 64 of reduced cross-sectional diameter, typically at a proximal end of the second generally cylindrical section 62 where transverse vibration of ultrasonic energy transmitted from the first generally cylindrical section is amplified. A conically tapered section 66 is preferably interposed between the first and second cylindrical sections. The ultrasound transmission wire includes a penultimate or third generally cylindrical section 70 of the ultrasound transmission wire distal to the second section and having a third cross-sectional diameter that is smaller than the second cross-sectional diameter, an amplification region 71 at the proximal end of the third generally cylindrical section, and a conically tapered section 72 disposed between he second and third generally cylindrical sections. An end or fourth generally cylindrical section 74 is provided on the ultrasound transmission wire distal to the third section and has a fourth cross-sectional diameter that is larger than the cross-sectional diameter of the third or penultimate cylindrical section 70 immediately adjacent and proximal to the end cylindrical section 74. A conically tapered section 76 is preferably interposed between the penultimate 70 and end 74 cylindrical sections.

In FIG. 3, a constraining member 78 is disposed around the amplification region 64, and extends approximately midway over the conically tapered section 66 and over a proximal portion of the second cylindrical section 62 to reduce transverse vibration. A distal or second constraining member 80 is disposed around the amplification region 71 of the third generally cylindrical section 70. In this embodiment, the second constraining member extends over a distal portion of the second cylindrical section 62, the conically tapered section 72, the smaller diameter penultimate cylindrical section 70, the conically tapered section 76, and a proximal portion of the end cylindrical section 74 to reduce transverse vibration at the amplification region of the third generally cylindrical section.

Another presently preferred embodiment is illustrated in FIG. 4, showing the same ultrasound transmission wire as in FIG. 3 with a configuration having a long constraining member. In this embodiment, a constraining member 82 is disposed over a proximal portion of the end cylindrical section 74, the smaller diameter penultimate cylindrical section 70, the conically tapered section 76 between them, the larger diameter cylindrical section 62 immediately adjacent and proximal to the penultimate cylindrical section 70, and the conically tapered section 72 immediately adjacent and proximal to the penultimate cylindrical section 70 as well as over the amplification region 64 and approximately midway over the conically tapered section 66. As should be readily apparent, the constraining member can be extended over more segments of increased amplification as well.

It has thus been demonstrated that the present invention provides for an ultrasound transmission wire for use in ultrasonic angioplasty having characteristics of improved flexibility, reduced attenuation of ultrasonic energy transmitted by the wire, and improved reduction of fracturing or breakage at areas of stress concentration, by providing constraining members at regions of amplification of transverse vibration that do not interfere with sonic propagation, tensile strength, and flexibility of the ultrasonic angioplasty transmission wire.

As discussed above, such a long constraining member can provide an additional source of friction that can degrade the longitudinal transmission of acoustic energy. However, this loss may be more than offset by the manufacturing convenience and lowered manufacturing cost resulting from the single, more easily locatable constraining member 82 shown in FIG. 4.

Figure 5:
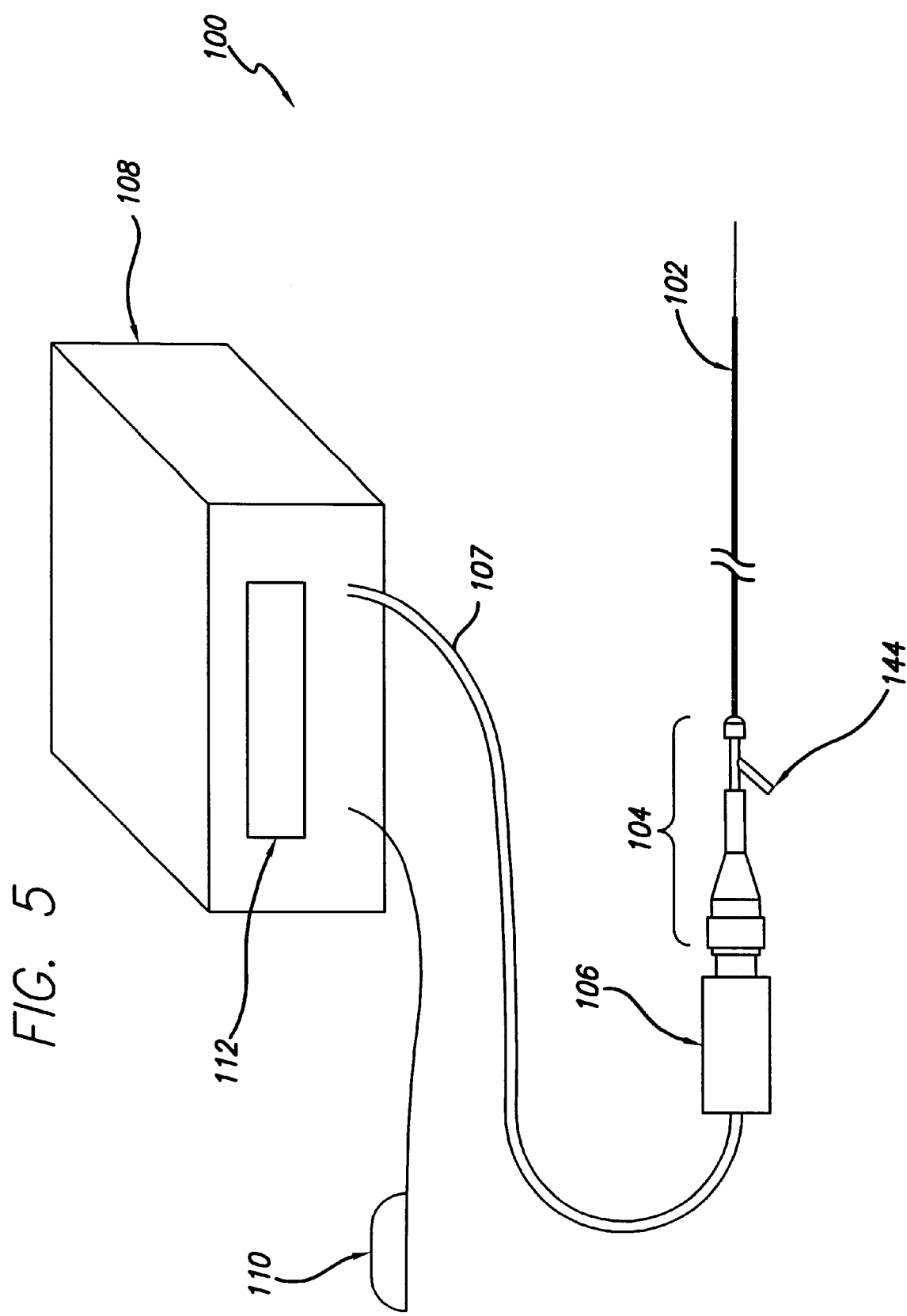
FIG. 5 is a general view of an angioplasty system incorporating an ultrasonic energy delivery catheter having an ultrasound transmission wire as shown in previous figures.

The perspective view in FIG. 5 is of an over-the-wire ultrasound catheter system 100 in which a catheter 102 has a proximal end connector assembly 104 mounted on the proximal end thereof. As used herein, the term "over-the-wire" shall refer to a catheter that has a guide wire passage lumen formed within the body of the catheter such that a flexible guide wire may be advanced through the body of the catheter and out of a guide wire passage aperture formed in the distal end of the catheter. Returning to FIG. 5, an ultrasound transducer 106 is connected to the proximal end of the proximal connector assembly 104. An ultrasound generator 108 having a foot-actuated on/off switch 110 is operatively connected to the ultrasound transducer 106 through an electrical cable 107 so as to send ultrasonic energy through the ultrasound catheter 102, when desired. The generator 108 includes a display 112 that presents certain information about the ultrasonic energy application process.

The distal end of the catheter 102 may include a dilatation balloon, a stent, or other apparatus depending on the configuration selected and is configured to be percutaneously inserted into a body vascular system and through tortuous body lumina to a desired location within the body vascular system. The catheter 102 includes an ultrasound transmission wire (not shown) as described above.

Figure 6:
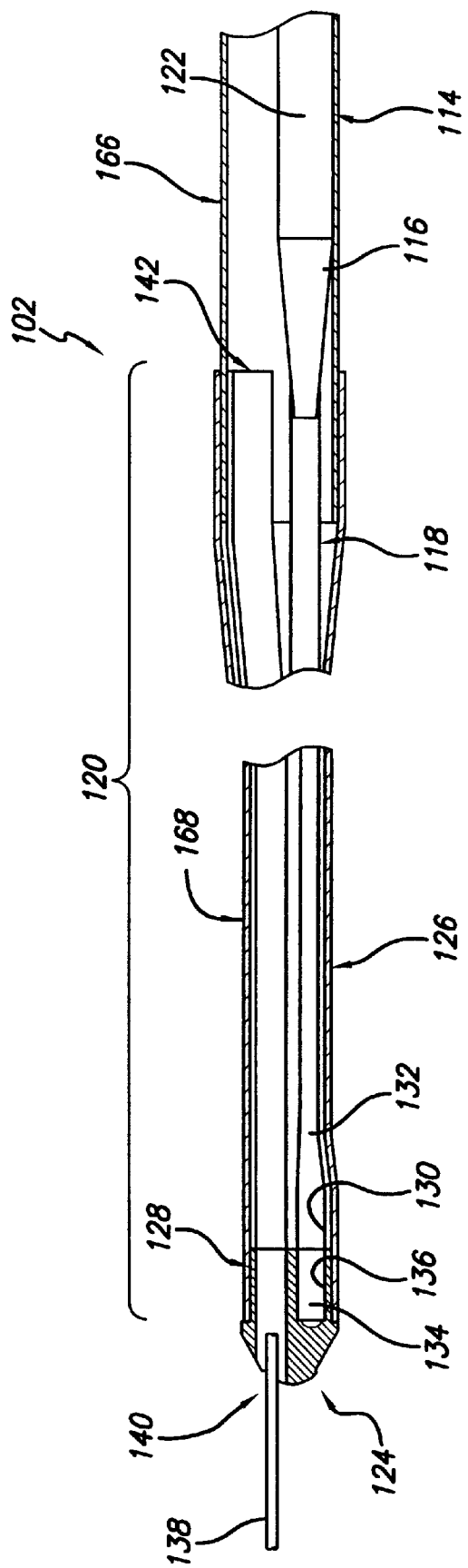
FIG. 6 is a sectional view of the distal end of a catheter showing a distal head configured to apply ultrasound energy to a blockage and having a guide wire aperture through which a guide wire may be positioned.

Turning now to FIG. 6, a sectional view of part of the catheter 102 is shown, which is an over-the-wire configuration. An ultrasound transmission member 114 includes tapering 116 for amplification at its distal end. The taper 116 terminates in a reduced diameter section 118 of the ultrasound transmission member 114. Because the reduced diameter distal portion 118 of the ultrasound transmission member 114 is of smaller cross-sectional diameter and less mass, it is more flexible and less rigid than the proximal portion thereof. In the embodiment of the catheter 102 shown in FIG. 6, the outer diameter of the distal portion 120 of the catheter is also reduced to coincide with the reduced diameter distal portion 116, 118 of the ultrasonic transmission member 114, and also will exhibit less rigidity and greater flexibility than the remainder of the catheter body.

The present embodiment further includes an optional improvement to the ultrasound transmission member 114, said improvement comprising the disposition of a low friction coating or jacket 122 on the outer surface of all or a portion of the ultrasound transmission member 114. The low friction coating or jacket 122 may be disposed on the outer surface of the ultrasound transmission member so as to completely cover the ultrasound transmission member along its entire length, or along a discrete region or regions thereof. Such coating or jacket 122 may comprise a layer of low friction polymer material such as polytetrafluoroethylene (ptfe) (Teflon™ Dupont, Inc., Wilmington, Del.) or other plastic materials such as polyethylene. The coating or jacket 122 may be applied as a liquid and subsequently allowed to cure or harden on the surface of the ultrasound transmission member 114. Alternatively, the coating or jacket 122 may be in the form of an elongate tube slidably disposable over the outer surface of the ultrasound transmission member. Such coating or jacket 122 serves to prevent or diminish friction between the outer surface of the ultrasound transmission member 114 and the adjacent structures of the catheter or proximal end connector assembly 104 through which the ultrasound transmission member 114 extends.

Although not shown, the ultrasound transmission member 114 of FIG. 6 may have one or more constraining members mounted on it, such as that indicated by numeral 48 in FIG. 2.

A distal head 124 is firmly bonded, attached, or connected to the catheter body 126 such that the distal head is prevented from undergoing longitudinal or transverse movement separate from or relative to the catheter body. Additionally, such affixation of the distal head to the catheter body increases the conveyance of ultrasound energy into the distal portion of the catheter body 126, thereby resulting in enhanced cavitation effects created by the distal portion of the catheter body. Such bonding connection or attachment of the distal head 124 to the catheter body 126 may be accomplished by any suitable means. One means of attaching the distal head 124 to the catheter body 126 is through the use of an adhesive.

In the embodiment shown in FIG. 6, the adhesive is applied to the neck portion 128 of the distal head 124 prior to insertion thereof into the distal end of the lumen 130 of the catheter body 126. The adhesive may comprise any suitable adhesive, such as cyanoacrylate (e.g. Loctite™, Loctite Corp., Ontario, CANADA or Dron Alpha™, Borden, Inc., Columbus, Ohio) or polyurethane (e.g. Dymax™, Dymax Engineering Adhesive, Torrington, Conn.) to firmly bond and attach the distal head 124 to the catheter body 126.

The distal head 124 may be formed of any suitable rigid material such as metal or plastic. In devices wherein the distal head is formed of plastic, the surrounding plastic catheter body 126 may be thoroughly welded, heat sealed, or solvent welded to the plastic distal head 124, in accordance with the types of plastics employed.

In the alternative to the use of adhesives, various mechanical or frictional connectors, such as screw threads, lugs or other surface modifications formed on the neck portion 128 of the distal head 124, may be utilized to hold the distal head 124 in a fixed position relative to the catheter body 126. In such embodiments, corresponding grooves, detents or surface modifications may also be formed in the surrounding inner wall of the catheter body 126 so as to cooperate with any such threads, lugs or other surface modifications formed on the opposing surface of the distal head 124. Such threads, lugs or other surface modifications will be configured and constructed so as to mechanically or frictionally hold the distal head 124 in fixed position relative to the catheter body 126.

The distal head 124 is preferably formed of radio dense material so as to be easily discernable by radiographic means. Accordingly, the distal head 124 may preferably be formed of metal or, alternatively, may be formed of plastic, ceramic or rubber materials, optionally having one or more radio dense markers fixed thereto or formed therein. For example, the distal head 124 may be molded of plastic such as acrylonitrile-butadiene-styrene (ABS) and one or more metallic foil strips or other radio opaque markers may be affixed to such plastic distal head 124 in order to impart sufficient radio density to permit the distal head to be readily located by radiographic means. Additionally, in embodiments wherein the distal head is formed of molded plastic or other non-metallic material, a quantity of radio dense filler such as powdered bismuth or $BaSO_4$ may be disposed within the plastic or other non-metallic material of which the distal head is formed so as to impart enhanced radio density to the distal head.

The ultrasound transmission member 114 is tapered outward 132 at its most distal extreme 134 to a size that fits within a cavity 136 formed in the distal head 124. Although this outward taper attenuates the ultrasonic energy somewhat, it results in greater stability of the ultrasound transmission member 114 at the distal end because there is more surface area provided for adhesive attachment to the distal head and less likelihood of breakage at the attachment point.

Another feature of the catheter 12 is shown in FIG. 6. At the distal end 120, two tubular members are joined to result in the catheter shaft. In particular, a first tubular member 166 is used for the proximal and center sections of the catheter shaft while a second tubular member 168 is used for the distal section 120. As shown, the second, distal, tubular member 168 overlaps the first tubular member 166. The two members may be held together with adhesive. Such configuration to the catheter enables more cost effective manufacturing techniques as well as greater accuracy in manufacturing the catheter.

Also shown in FIG. 6 is a guide wire 138 disposed in a guide wire aperture 140 formed in the distal head 124. The catheter body may include a separate guide wire lumen 142 within which the guide wire is disposed. The guide wire may be introduced and retracted from the catheter body through a side arm 144 shown in FIG. 5. This configuration is referred to as an over-the-wire ("OTW") catheter arrangement.

Figure 7:
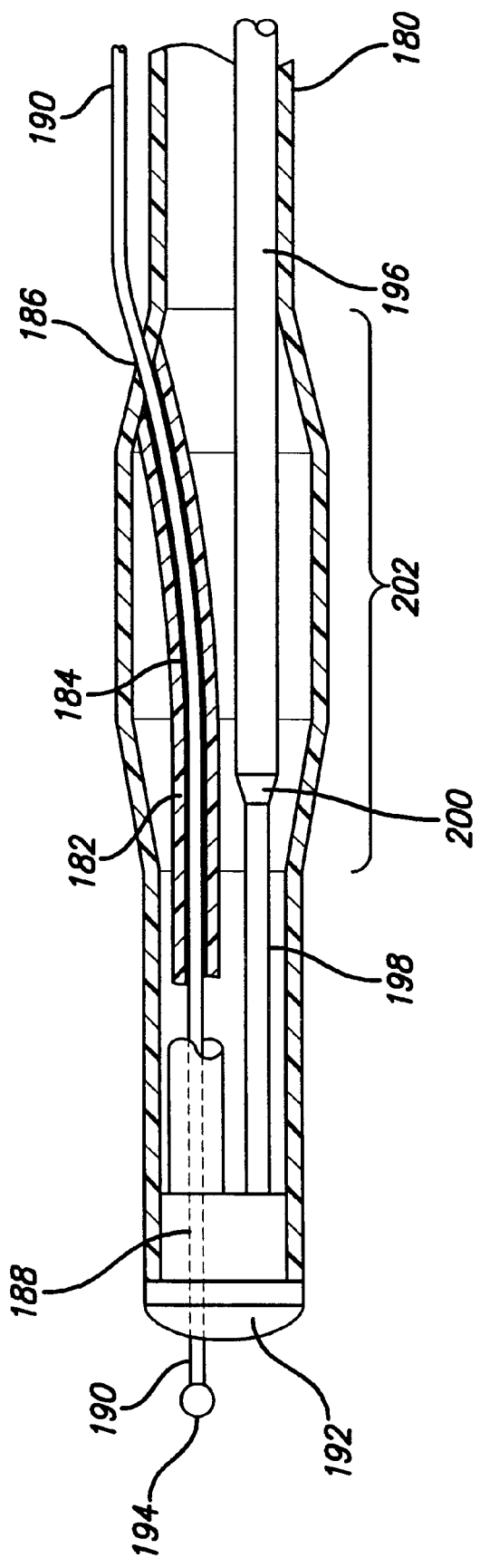
FIG. 7 is a diagram of a rapid exchange ("RX") catheter using the ultrasound angioplasty transmission member of FIG. 1, and showing various details of the ultrasound catheter distal end.

Turning now to FIG. 7, a rapid exchange or "RX" embodiment of a catheter is shown. In this embodiment, the catheter body 180 may be provided with a distal guide wire passage tube 182 positioned within the inner bore or lumen 184 of the catheter body 180 and extending from a guide wire re-entry aperture 186 to the guide wire passage aperture 188 formed in the distal head 192 of the device. As such, the proximal end member (not shown) of a guide wire 190 may be inserted into the distal head 192 of the catheter body 180 through the guide wire passage aperture 188 and subsequently disposed in a proximal direction through the guide wire lumen 184 of the guide wire tube 182 to a point where the proximal end of the guide wire 190 emerges from the guide wire entry/re-entry aperture 186. After emerging from the guide were entry/re-entry aperture 186, the proximal portion (not shown) of the guide wire 190 may extend and/or reside adjacent the outer surface of the proximal portion (not shown) of the catheter body 180. The catheter body 180 and the guide wire 190 may then be distally and/or proximally repositioned, relative to one another, during the procedure. Also, if desired, the guide wire 190 may be fully withdrawn and extracted by pulling the guide wire in a proximal direction such that the distal tip 194 of the guide wire is pulled through the distal head 192, through the guide wire passage tube 182, and out of the guide wire entry/reentry aperture 186, and the guide wire 190 is subsequently fully withdrawn from the catheter body 180, leaving only the ultrasound catheter in place in the patient.

The distal portion of the catheter shown in FIG. 7 contains many of the same elements shown in other figures. In particular, the distal head 192 is fixedly attached to the catheter body 180 through adhesive or other means. An ultrasound angioplasty transmission member 196 such as that shown in FIG. 6 above is attached to the distal head 192 and has a stepped down length 198 with a conical transition area 200. An enlarged area 202 of the distal portion is used to accommodate the additional guide wire tube 182 in this RX embodiment.

Although not shown, the ultrasound transmission member 196 may have one or more constraining members mounted on it, such as that indicated by numeral 48 in FIG. 2.

Although embodiments shown and described herein include OTW and RX catheters, other embodiments are possible that include combinations or hybrids of OTW and RX. As is apparent, an RX catheter system is also easily used with the ultrasound angioplasty transmission member described and shown.

Although the invention has been described herein with specific reference to presently preferred embodiments thereof, it will be appreciated by those skilled in the art that various additions, modifications, deletions and alterations may be made to such preferred embodiments thereof without departing from the spirit and scope of the invention. Accordingly, it is intended that the invention not be limited, except as by the appended claims.

What is claimed is:

1. An ultrasound transmission member for use in an ultrasonic angioplasty device, the ultrasound transmission member having a proximal end configured to be connected to an ultrasound transducer and a distal end for applying ultrasonic energy to an area of vascular blockage, and the ultrasound transmission member having a distal portion with at least one amplification region of reduced cross-sectional diameter where transverse vibration of ultrasonic energy transmitted by the ultrasound transmission member is amplified, the ultrasound transmission member comprising:

a constraining member comprising an annular band tightly disposed around the amplification region such that it is firmly contacting the amplification region to reduce transverse vibration at the amplification region, to thereby lower stress and reduce fractures of the ultrasound transmission member while allowing longitudinal movement of the ultrasound transmission member.

2. The ultrasound transmission member of claim 1 wherein the ultrasound transmission member comprises a first generally cylindrical section of the ultrasound transmission member having a first cross-sectional diameter, and a second generally cylindrical section of the ultrasound transmission member distal to the first section and having a second cross-sectional diameter that is smaller than the first cross-sectional diameter, the amplification region being formed at a proximal portion of the second generally cylindrical section.

3. The ultrasound transmission member of claim 2 further comprising a conically tapered section interposed between the first and second cylindrical sections.

4. The ultrasound transmission member of claim 1 further comprising a plurality of generally cylindrical sections, each of the plurality of generally cylindrical sections having reduced cross-sectional diameter relative to a proximal adjacent section resulting in a plurality of amplification regions in the cylindrical sections of reduced cross-sectional diameter, wherein the constraining member is disposed around at least one of the amplification regions of the reduced diameter cylindrical sections to reduce transverse vibration at the amplification regions.

5. The ultrasound transmission member of claim 4 further comprising a plurality of conically tapered sections interposed between adjacent ones of the plurality of generally cylindrical sections.

6. The ultrasound transmission member of claim 1 wherein the ultrasound transmission member comprises an end cylindrical section, a penultimate cylindrical section immediately adjacent and proximal to the end cylindrical section, and a cylindrical section immediately adjacent and proximal to the penultimate cylindrical section having a larger diameter than the penultimate cylindrical section, the end cylindrical section having a cross-sectional diameter that is larger than the penultimate cylindrical section, and the constraining member being disposed over the end cylindrical section and over the penultimate cylindrical section and over the larger diameter cylindrical section immediately adjacent and proximal to the penultimate cylindrical section.

7. The ultrasound transmission member of claim 1 wherein the ultrasound transmission member comprises an end cylindrical section, a penultimate cylindrical section immediately adjacent and proximal to the end cylindrical section, the end cylindrical section having a cross-sectional diameter that is larger than the penultimate cylindrical section, a larger cylindrical section immediately adjacent and proximal to the penultimate cylindrical section having a larger diameter than the penultimate cylindrical section, and a conically tapered section immediately adjacent and proximal to the larger cylindrical section, and the constraining member being disposed over the end cylindrical section and over the penultimate cylindrical section and over the larger diameter cylindrical section immediately adjacent and proximal to the penultimate cylindrical section and over the conically tapered section immediately adjacent and proximal to the larger diameter cylindrical section.

8. The ultrasonic angioplasty catheter device of claim 7 further characterized in that the region of reduced cross-sectional diameter is located within 5 cm to 30 cm of the distal end of the ultrasound transmission member.

9. The ultrasound transmission member of claim 1 wherein the constraining member is formed of a non-metallic material.

10. The ultrasound transmission member of claim 9 wherein the constraining member is formed of shrink tubing.

11. The ultrasound transmission member of claim 9 wherein the constraining member is formed of rubber.

12. The ultrasound transmission member of claim 9 wherein the constraining member is formed of plastic.

13. An ultrasound transmission wire for use in an ultrasonic angioplasty device, the ultrasound transmission wire having a proximal end configured to attach to an ultrasound transducer and a distal end for applying ultrasonic energy to an area of vascular blockage, the ultrasound transmission wire comprising:

a first generally cylindrical section of the ultrasound transmission wire having a first cross-sectional diameter;

a second generally cylindrical section of the ultrasound transmission wire distal to the first section and having a second cross-sectional diameter that is smaller than the first cross-sectional diameter, the second generally cylindrical section having an amplification region where transverse vibration of ultrasonic energy transmitted from the first generally cylindrical section is amplified; and a constraining member comprising an annular band tightly disposed around the amplification region of the second generally cylindrical section such that it is firmly contacting the amplification region to reduce transverse vibration at the amplification region, to thereby lower stress and reduce ultrasonic wire fractures of the ultrasound transmission wire, while allowing longitudinal movement of the ultrasound transmission wire.

14. The ultrasound transmission wire of claim 13 wherein the amplification region is at a proximal end of the second generally cylindrical section.

15. The ultrasound transmission wire of claim 13 further comprising a conically tapered section interposed between the first and second generally cylindrical sections.

16. The ultrasound transmission wire of claim 13 further comprising a third generally cylindrical section of the ultrasound transmission wire distal to the second section and having a third cross-sectional diameter that is smaller than the second cross-sectional diameter, the third generally cylindrical section having an amplification region.

17. The ultrasound transmission wire of claim 16 further comprising a conically tapered section interposed between the second and third generally cylindrical sections.

18. The ultrasound transmission wire of claim 16 further comprising a second constraining member disposed around the amplification region of the third generally cylindrical section to reduce transverse vibration at the amplification region of the third generally cylindrical section, to thereby lower stress and reduce ultrasonic wire fractures of the ultrasound transmission wire, while allowing longitudinal movement of the ultrasound transmission wire.

19. The ultrasound transmission wire of claim 18 further comprising a fourth generally cylindrical section of the ultrasound transmission wire distal to the third section and having a fourth cross-sectional diameter that is larger than the third cross-sectional diameter.

20. The ultrasound transmission wire of claim 19 wherein the second constraining member is disposed over a distal portion of the second generally cylindrical section, the third generally cylindrical section, and the fourth generally cylindrical section.

21. The ultrasound transmission wire of claim 19 wherein the second constraining member is disposed over a distal portion of the first conically tapered section, the second generally cylindrical section, the third generally cylindrical section, and the fourth generally cylindrical section.

22. The ultrasound transmission wire of claim 21 wherein the constraining member is formed of a material selected from the group consisting of shrink tubing, rubber, and plastic.

23. The ultrasound transmission member of claim 13 wherein the constraining member is formed of a non-metallic material.

24. An ultrasonic angioplasty catheter device comprising an elongate flexible catheter having a proximal end, a distal end, and at least one lumen extending longitudinally therethrough, the device comprising:

an ultrasound transmission member extending through said lumen and having a distal end with a head for applying ultrasonic energy to an occlusive lesion, and a proximal end configured to be connected to an ultrasound generating device, the ultrasound transmission member having a distal portion with at least one amplification region of reduced cross-sectional diameter where transverse vibration of ultrasonic energy transmitted by the ultrasound transmission member is amplified;

wherein the ultrasound transmission member comprises a constraining member a constraining member comprising an annular band tightly disposed around the amplification region such that it is firmly contacting the amplification region to reduce transverse vibration at the amplification region to thereby lower stress and reduce fractures of the ultrasound transmission member while allowing longitudinal movement of the ultrasound transmission member.

25. The ultrasonic angioplasty catheter device of claim 24 wherein the ultrasonic transmission member is in a fixed position within the catheter lumen and is connected to a distal head positioned on the distal end of said ultrasound member such that the distal head extends beyond the distal end of the catheter.

26. The ultrasonic angioplasty catheter device of claim 25 wherein the distal head comprises a guide wire aperture to permit passage of a guide wire therethrough.

27. The ultrasonic angioplasty catheter device of claim 24 wherein the distal head comprises a larger diameter distal portion positioned beyond the distal end of the catheter and a smaller diameter portion located between the distal portion and the ultrasound transmission member and extending within the catheter.

28. The ultrasonic angioplasty catheter device of claim 24 wherein the ultrasound transmission member is formed at least partially of a superelastic metal alloy.

29. The ultrasonic angioplasty catheter device of claim 24 wherein the ultrasound transmission member is formed at least partially of a shape memory alloy that exhibits superelastic properties when in its martensitic state.

30. The ultrasonic angioplasty catheter device of claim 24 wherein the ultrasound transmission member is formed of a nickel-titanium alloy.

31. The ultrasonic angioplasty catheter device of claim 24 wherein the ultrasound transmission member has a smaller diameter towards its distal end and increases to a larger diameter towards its proximal end.

32. The ultrasonic angioplasty catheter device of claim 24 wherein the ultrasound transmission member comprises a first generally cylindrical section of the ultrasound transmission member having a first cross-sectional diameter, and a second generally cylindrical section of the ultrasound transmission member distal to the first section and having a second cross-sectional diameter that is smaller than the first cross-sectional diameter, the amplification region being formed at a proximal portion of the second generally cylindrical section.

33. The ultrasonic angioplasty catheter device of claim 24 further comprising a plurality of generally cylindrical sections, each of the plurality of generally cylindrical sections having reduced cross-sectional diameter relative to a proximal adjacent section resulting in a plurality of amplification regions in the cylindrical sections of reduced cross-sectional diameter, wherein the constraining member is disposed around at least one of the amplification regions of the reduced diameter cylindrical sections to reduce transverse vibration at the amplification regions.

34. The ultrasonic angioplasty catheter device of claim 33 further comprising a conically tapered section interposed between the first and second cylindrical sections.

35. The ultrasonic angioplasty catheter device of claim 34 further comprising a plurality of conically tapered sections interposed between adjacent ones of the plurality of generally cylindrical sections.

36. The ultrasonic angioplasty catheter device of claim 24 wherein the ultrasound transmission member comprises an end cylindrical section, a penultimate cylindrical section immediately adjacent and proximal to the end cylindrical section, and a cylindrical section immediately adjacent and proximal to the penultimate cylindrical section having a larger diameter than the penultimate cylindrical section, the end cylindrical section having a cross-sectional diameter that is larger than the penultimate cylindrical section, and the constraining member being disposed over the end cylindrical section and over the penultimate cylindrical section and over the larger diameter cylindrical section immediately adjacent and proximal to the penultimate cylindrical section.

37. The ultrasonic angioplasty catheter device of claim 24 wherein the ultrasound transmission member comprises an end cylindrical section, a penultimate cylindrical section immediately adjacent and proximal to the end cylindrical section, the end cylindrical section having a cross-sectional diameter that is larger than the penultimate cylindrical section, a larger cylindrical section immediately adjacent and proximal to the penultimate cylindrical section having a larger diameter than the penultimate cylindrical section, and a conically tapered section immediately adjacent and proximal to the larger cylindrical section, and the constraining member being disposed over the end cylindrical section and over the penultimate cylindrical section and over the larger diameter cylindrical section immediately adjacent and proximal to the penultimate cylindrical section and over the conically tapered section immediately adjacent and proximal to the larger diameter cylindrical section.

38. The ultrasonic angioplasty catheter device of claim 37 wherein the constraining member is formed of plastic.

39. The ultrasonic angioplasty catheter device of claim 24 wherein the constraining member is formed of a non-metallic material.

40. The ultrasonic angioplasty catheter device of claim 24 wherein the constraining member is formed of shrink tubing.

41. The ultrasonic angioplasty catheter device of claim 24 wherein the constraining member is formed of rubber.

* * * * *